(12) United States Patent
Innis et al.

(10) Patent No.: US 6,174,721 B1
(45) Date of Patent: *Jan. 16, 2001

(54) CHIMERIC PROTEINS

(75) Inventors: Michael A. Innis, Moraga; Abla A. Creasey, Piedmont, both of CA (US)

(73) Assignee: Chiron Corporation, Emeryville, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/943,682

(22) Filed: Oct. 14, 1997

Related U.S. Application Data

(63) Continuation of application No. 08/438,184, filed on May 9, 1995, now abandoned, which is a continuation of application No. 08/286,521, filed on Aug. 5, 1994, now Pat. No. 5,589,359.

(51) Int. Cl.[7] .................... C12N 15/62; C12N 15/63; C07K 14/745
(52) U.S. Cl. .................. 435/320.1; 536/23.4; 530/350; 530/380; 530/381
(58) Field of Search .................. 435/69.7, 69.6, 435/69.2, 320.1, 172.3, 440, 455, 471; 530/350, 380, 395, 381; 536/23.4

(56) References Cited

U.S. PATENT DOCUMENTS 5,589,359 * 12/1996 Innis et al. .................. 435/69.2

* cited by examiner

*Primary Examiner*—Karen Cochrane Carlson
*Assistant Examiner*—Gabriele E. Bugaisky
(74) *Attorney, Agent, or Firm*—Banner and Witcoff; Paul Savereide; Robert P. Blackburn

(57) ABSTRACT

Chimeric proteins possessing Kunitz-type domain 1 of TFPI-2 and Kunitz-type domain 2 of TFPI are disclosed, as are muteins of TFPI and TFPI-2. Nucleic acid sequences, expression vectors and transformed host cells encoding and capable of producing the disclosed chimeric proteins and muteins are also disclosed. Finally, methods for prevention and treatment of septic shock using the chimeric proteins and muteins are disclosed.

19 Claims, 4 Drawing Sheets

SEQUENCE LISTING (1) GENERAL INFORMATION:

(iii) NUMBER OF SEQUENCES: 37

(2) INFORMATION FOR SEQ ID NO:1:

```
        (i) SEQUENCE CHARACTERISTICS:
            (A) LENGTH: 51 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:1:

Cys Ala Phe Lys Ala Asp Asp Gly Pro Cys Lys Ala Ile Met Lys Arg
 1               5                  10                  15

Phe Phe Phe Asn Ile Phe Thr Arg Gln Cys Glu Glu Phe Ile Tyr Gly
                20                  25                  30

Gly Cys Glu Gly Asn Gln Asn Arg Phe Glu Ser Leu Glu Glu Cys Lys
             35                  40                  45

Lys Met Cys
         50

(2) INFORMATION FOR SEQ ID NO:2:

(i) SEQUENCE CHARACTERISTICS:
            (A) LENGTH: 51 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:2:

Cys Leu Leu Pro Leu Asp Tyr Gly Pro Cys Arg Ala Leu Leu Leu Arg
 1               5                  10                  15

Tyr Tyr Tyr Asp Arg Tyr Thr Gln Ser Cys Arg Gln Phe Leu Tyr Gly
                20                  25                  30

Gly Cys Glu Gly Asn Ala Asn Asn Phe Tyr Thr Trp Glu Ala Cys Asp
             35                  40                  45

Asp Ala Cys
         50

(2) INFORMATION FOR SEQ ID NO:3:

(i) SEQUENCE CHARACTERISTICS:
            (A) LENGTH: 51 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Cys Phe Leu Glu Glu Asp Pro Gly Ile Cys Arg Gly Tyr Ile Thr Arg
 1               5                  10                  15

Tyr Phe Tyr Asn Asn Gln Thr Lys Gln Cys Glu Arg Phe Lys Tyr Gly
                20                  25                  30

Gly Cys Leu Gly Asn Met Asn Asn Phe Glu Thr Leu Glu Glu Cys Lys
             35                  40                  45

Asn Ile Cys
         50

(2) INFORMATION FOR SEQ ID NO:4:

(i) SEQUENCE CHARACTERISTICS:
            (A) LENGTH: 54 amino acids
            (B) TYPE: amino acid
```

(C) STRANDEDNESS: single
        (D) TOPOLOGY: linear (ii) MOLECULE TYPE: peptide (xi) SEQUENCE DESCRIPTION: SEQ ID NO:4:

Cys Arg Leu Gln Val Ser Val Asp Asp Gln Cys Glu Gly Ser Thr Glu
1               5                   10                  15

Lys Tyr Phe Phe Asn Leu Ser Ser Met Thr Cys Glu Lys Phe Phe Ser
            20                  25                  30

Gly Gly Cys His Arg Asn Arg Ile Glu Asn Arg Phe Pro Asp Glu Ala
        35                  40                  45

Thr Cys Met Gly Phe Cys
    50

(2) INFORMATION FOR SEQ ID NO:5:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Cys Leu Thr Pro Ala Asp Arg Gly Leu Cys Arg Ala Asn Glu Asn Arg
1               5                   10                  15

Phe Tyr Tyr Asn Ser Val Ile Gly Lys Cys Arg Pro Phe Lys Tyr Ser
            20                  25                  30

Gly Cys Gly Gly Asn Glu Asn Asn Phe Thr Ser Lys Gln Glu Cys Leu
        35                  40                  45

Arg Ala Cys
    50

(2) INFORMATION FOR SEQ ID NO:6:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Cys Tyr Ser Pro Lys Asp Glu Gly Leu Cys Ser Ala Asn Val Thr Arg
1               5                   10                  15

Tyr Tyr Phe Asn Pro Arg Tyr Arg Thr Cys Asp Ala Phe Thr Tyr Thr
            20                  25                  30

Gly Cys Gly Gly Asn Asp Asn Asn Phe Val Ser Arg Glu Asp Cys Lys
        35                  40                  45

Arg Ala Cys
    50

(2) INFORMATION FOR SEQ ID NO:7:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Lys Lys Gly Phe Ile Gln Arg Ile Ser Lys Gly Gly Leu Ile Lys Thr
1               5                   10                  15

Lys Arg Lys Arg Lys Lys Gln Arg Val Lys Ile Ala Tyr Glu Glu Ile
            20                  25                  30

Phe Val Lys Asn Met
        35

(2) INFORMATION FOR SEQ ID NO:8:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Ala Lys Ala Leu Lys Lys Lys Lys Met Pro Lys Leu Arg Phe Ala
1               5                   10                  15

Ser Arg Ile Arg Lys Ile Arg Lys Lys Gln Phe
            20                  25

(2) INFORMATION FOR SEQ ID NO:9:

(i) SEQUENCE CHARACTERISTICS:
        (A) LENGTH: 276 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Arg Ala Ile Met Lys Arg Phe Phe Phe Asn Ile Phe Thr
            35                  40                  45

Arg Gln Cys Glu Glu Phe Ile Tyr Gly Gly Cys Glu Gly Asn Gln Asn
50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
            85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
            130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
            165                 170                 175

Val Pro Ser Leu Phe Glu Phe His Gly Pro Ser Trp Cys Leu Thr Pro
            180                 185                 190

```
Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
        210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
        275

(2) INFORMATION FOR SEQ ID NO:10:

(i) SEQUENCE CHARACTERISTICS:
         (A) LENGTH: 23 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:10:

Lys Thr Lys Arg Lys Arg Lys Lys Gln Arg Val Lys Ile Ala Tyr Glu
1               5                   10                  15

Glu Ile Phe Val Lys Asn Met
            20

(2) INFORMATION FOR SEQ ID NO:11:

(i) SEQUENCE CHARACTERISTICS:
         (A) LENGTH: 23 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:11:

Lys Lys Lys Lys Lys Met Pro Lys Leu Arg Phe Ala Ser Arg Ile Arg
1               5                   10                  15

Lys Ile Arg Lys Lys Gln Phe
            20

(2) INFORMATION FOR SEQ ID NO:12:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:12:

Ala Lys Leu Asn Cys Arg Leu Tyr Arg Lys Ala Asn Lys Ser Ser Lys
1               5                   10                  15

Leu (2) INFORMATION FOR SEQ ID NO:13:

(i) SEQUENCE CHARACTERISTICS:
```

(A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Thr Ser Asp Gln Ile His Phe Phe Phe Ala Lys Leu Asn Cys Arg
1               5                   10                  15

(2) INFORMATION FOR SEQ ID NO:14:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Ser Glu Lys Thr Leu Arg Lys Trp Leu Lys Met Phe Lys Lys Arg Glu
1               5                   10                  15

Leu Glu Glu Tyr
            20

(2) INFORMATION FOR SEQ ID NO:15:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

His Arg His His Pro Arg Glu Met Lys Lys Arg Val Glu Asp Leu
1               5                   10                  15

(2) INFORMATION FOR SEQ ID NO:16:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Phe Arg Lys Leu Thr His Arg Leu Phe Arg Arg Asn Phe Gly Tyr Thr
1               5                   10                  15

Leu Arg (2) INFORMATION FOR SEQ ID NO:17:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Leu Tyr Lys Lys Ile Leu Lys Lys Leu Leu Glu Ala (2) INFORMATION FOR SEQ ID NO:18:

(i) SEQUENCE CHARACTERISTICS:
      (A) LENGTH: 26 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:18:

Asn Gly Leu Lys Arg Asp Lys Leu Gly Cys Glu Tyr Cys Glu Cys Arg
1               5                  10                  15

Pro Lys Arg Lys Leu Ile Pro Arg Leu Ser
            20                  25

(2) INFORMATION FOR SEQ ID NO:19:

(i) SEQUENCE CHARACTERISTICS:
      (A) LENGTH: 161 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:19:

Asp Ser Glu Glu Asp Glu Glu His Thr Ile Ile Thr Asp Thr Glu Leu
1               5                  10                  15

Pro Pro Leu Lys Leu Met His Ser Phe Cys Ala Phe Lys Ala Asp Asp
            20                  25                  30

Gly Pro Cys Arg Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Gln Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr (2) INFORMATION FOR SEQ ID NO:20:

(i) SEQUENCE CHARACTERISTICS:
      (A) LENGTH: 9 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "Adapter"

(xi) SEQUENCE DESCRIPTION: SEQ ID NO:20:

CCGCGGGGC                                                                          9

(2) INFORMATION FOR SEQ ID NO:21:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:21:

GCTCCGCGGT GGCGATTCTG AGGAGGAGAT GAAGAAC                                            37

(2) INFORMATION FOR SEQ ID NO:22:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:22:

TCTGTCGACT CACATATTTT TAACAAAAAT TTCTTCAT                                           38

(2) INFORMATION FOR SEQ ID NO:23:

(i) SEQUENCE CHARACTERISTICS:
        (A) LENGTH: 13 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "adapter"

(xi) SEQUENCE DESCRIPTION: SEQ ID NO:23:

TCTAGATAAA AGA                                                                     13

(2) INFORMATION FOR SEQ ID NO:24:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:24:

ATCTCTAGAT AAAAGAGATT CTGAGGAAGA TGAAGAAC                                           38

(2) INFORMATION FOR SEQ ID NO:25:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:25:

TCTGTCGACT CAGGTTCCAT AATTATCCAC CT                32

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:26:

AGGTATTTTT ATAACAATCA GACAAAACAG TGT                33

(2) INFORMATION FOR SEQ ID NO:27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:27:

GAAACGTTCA CACTGTTTTG TCTGATTGTT ATA                33

(2) INFORMATION FOR SEQ ID NO:28:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:28:

CCAGCTCAAT GCTGTGAATA ACTCCCTGAC TCCG               34

(2) INFORMATION FOR SEQ ID NO:29:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:29:

CTTGGTTGAT TGCGGAGTCA GGGAGTTATT CACAGC             36

(2) INFORMATION FOR SEQ ID NO:30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:30:

GGGGGAAATG AAAACAATTT TACTTCCAAA CAA                           33

(2) INFORMATION FOR SEQ ID NO:31:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:31:

CCTCAGACAT TCTTGTTTGG AAGTAAAATT GTTTTC                        36

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:32:

CCGATGCATT CATTTTGTGC ATTC                                     24

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:33:

CCTCATGATT GCCCGACATG GGCC                                     24

(2) INFORMATION FOR SEQ ID NO:34:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:34:

GGTCCGCGGT GGTGATGCTG CTCAGGAGC                                29

(2) INFORMATION FOR SEQ ID NO:35:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid

```
            (A) DESCRIPTION: /desc = "primer"

(xi) SEQUENCE DESCRIPTION: SEQ ID NO:35:

GCAATGTTGT TTTTTCTATC CTCCAGCAAG CAT                              33

(2) INFORMATION FOR SEQ ID NO:36:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:36:

GGATAGAAAA AAACAACATT GCAACAAGAA AAGC                             34

(2) INFORMATION FOR SEQ ID NO:37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:37:

GGTTCTTGCA TTCTTCCAGT GTCTCAAAAT TG                               32
```

CHIMERIC PROTEINS

This application is a continuation of application Ser. No. 08/438,184, filed May 9, 1995, now abandoned which is a continuation of application Ser. No. 08/286,521, filed Aug. 5, 1994, now U.S. Pat. No. 5,589,359.

BACKGROUND OF THE INVENTION

This invention relates to chimeric proteins capable of simultaneously binding and inhibiting factor VIIa/tissue factor complex (factor VIIa/TF complex) and factor Xa, expression vectors coding for the proteins of the invention, host cells transformed with the expression vectors, methods for producing the proteins, pharmaceutical compositions containing the proteins, methods of treatment or prevention of septic shock using the proteins, methods of inhibiting coagulation disorders and monoclonal antibodies against the proteins.

Human Tissue Factor Pathway Inhibitor (TFPI) is a plasma protease inhibitor. Based on homology study, TFPI appears to be a member of the Kunitz-type basic protease inhibitor gene superfamily. TFPI functions in at least two ways: 1) Inhibition of the catalytic activity of factor VIIa/TF complex and 2) By binding to the active site of factor Xa. The primary sequence of TFPI, deduced from its cDNA sequence, indicates that the protein contains three Kunitz-type domains. The first of these, Kunitz-type domain 1, is believed to be required for the efficient binding to and inhibition of factor VIIa/TF complex, which is enhanced by the presence of the second Kunitz-type domain, Kunitz-type domain 2. Kunitz-type domain 2 is required for the efficient binding to and inhibition of factor Xa by TFPI. The function of the third Kunitz-type domain, Kunitz-type domain 3, is unknown. TFPI has no known enzymatic activity and probably inhibits the activity of protease targets in a stoichiometric manner, namely, binding of one Kunitz-type domain to the active site of one protease molecule. TFPI is also known as Lipoprotein Associated Coagulation Inhibitor (LACI), tissue factor inhibitor (TFI) and extrinsic pathway inhibitor (EPI).

Mature TFPI is a polypeptide of about 276 amino acids in length with a negatively charged amino terminal end and a positively charged carboxyl terminal end. The C-terminal tail (i.e., the sequence following the last cysteine residue of Kunitz-type domain 3) is highly basic and is believed to aid in the localization of TFPI to cell surfaces by binding to glycosaminoglycan (including heparin) or phospholipids found on cell surfaces. This cell surface localization property is believed to be important for full anticoagulant activity and for optimal inhibition of factor Xa TFPI contains 18 cysteine residues and forms 9 disulfide bridges when correctly folded. The primary sequence contains three Asn-X-Ser/Thr N-linked glycosylation consensus sites with asparagine residues at positions 145, 196, and 256. The carbohydrate component of mature TFPI is approximately 30% of the mass of the protein. Data from proteolytic mapping and mass spectral data imply that the native carbohydrate moieties are heterogeneous. Native TFPI is also found to be phosphorylated at the serine residue at position 2 of the protein to varying degrees. The role of phosphorylation at Ser-2 in TFPI function has yet to be elucidated.

Recently, another protein with a high degree of structural and functional similarity to TFPI has been identified, as described in Sprecher et al. *Proc. Natl. Acad. Sci. USA* 91:3353–3357 (1994). The predicted secondary structure of this 213 amino acid residue protein, called TFPI-2, is virtually identical to TFPI having three Kunitz-type domains, 9 disulfide bridges, an acidic amino terminus and a basic carboxy terminus. The three Kunitz-type domains of TFPI-2 exhibit 43%, 35% and 53% primary sequence identity with TFPI Kunitz-type domains 1, 2, and 3, respectively. Compared with TFPI, recombinant TFPI-2 strongly inhibits the amidolytic activity of factor VIIa/TF complex and weakly inhibits factor Xa activity. TFPI-2 is reported to bind with greater affinity to factor VIIa/TF complex than does TFPI, whereas TFPI binds to factor Xa with greater affinity than does TFPI-2.

The presumed P1-reactive site in Kunitz-type domain 1 of TFPI-2 is arginine, as contrasted with lysine in TFPI. The P1-reactive site in Kunitz-domain 2 of TFPI-2 is glutamate, as contrasted with arginine in TFPI. Also, the Kunitz-type domain 2 of TFPI-2 contains two additional amino acid residues between the fourth and fifth cysteine residues. The spacer region between Kunitz-type domains 1 and 2 in TFPI-2 is much shorter than the corresponding TFPI spacer region. One or more of these differences may result in the different affinities of the two proteins for factor VIIa/TF complex and Xa.

TFPI has been shown to prevent mortality in a lethal *Escherichia coli* (*E. coli*) septic shock baboon model. Creasey et al, *J. Clin. Invest.* 91:2850–2860 (1993). Administration of TFPI at 6 mg/kg body weight shortly after infusion of a lethal dose of *E. coli* resulted in survival in all five TFPI-treated animals with significant improvement in quality of life, compared with a mean survival time for the five control animals of 39.9 hours. The administration of TFPI also resulted in significant attenuation of the coagulation response, of various measures of cell injury and significant reduction in pathology normally observed in *E. coli* sepsis target organs, including kidneys, adrenal glands, and lungs. Due to its clot-inhibiting properties, TFPI may also be used to prevent problems associated with thrombosis and clotting such as during microvascular surgery. For example, U.S. Pat. No. 5,276,015 discloses the use of TFPI in a method for reducing thrombogenicity of microvascular anastomoses wherein TFPI is administered at the site of the microvascular anastomoses contemporaneously with microvascular reconstruction.

TFPI has been isolated from human plasma and from human tissue culture cells, including HepG2, Chang liver and SK hepatoma cells. Recombinant TFPI has been expressed in mouse C127 cells, baby hamster kidney cells, Chinese hamster ovary cells and human SK hepatoma cells. Recombinant TFPI from the mouse C127 cells has been shown in animal models to inhibit tissue-factor induced coagulation. A non-glycosylated form of recombinant TFPI has also been produced and isolated from *Escherichia coli* (*E. coli*) cells as disclosed in U.S. Pat. No. 5,212,091. This form of TFPI has been shown to be active in the inhibition of bovine factor Xa and in the inhibition of human tissue factor-induced coagulation in plasma. In some assays, the *E. coli*-produced TFPI has been shown to be more active than TFPI derived from SK hepatoma cells. Methods have been disclosed for purification of recombinant TFPI from yeast cell culture medium, such as in Petersen et al, *J. Biol. Chem.* 18:13344–13351 (1993). Truncated forms of recombinant TFPI have also been studied, as described in Hamamoto et al. *J. Biol. Chem.* 268:8704–8710 (1993) and Petersen et al. ibid.

Petersen et al. ibid have attempted to produce TFPI and variants of TFPI, including: 1) variants of TFPI in which the complete C-terminal one third of the polypeptide, including Kunitz-type domain 3, was deleted; 2) variants of TFPI in which just Kunitz-type domain 3 was deleted; and 3) variants of TFPI in which the basic portion of the peptide, C-terminal to Kunitz-type domain 3, were deleted. They found that high yields were obtained only with the first variant. This variant was heterogeneously glycosylated, and its anti-coagulant activity was 5–50 fold lower than full-length TFPI obtained from mammalian cells.

A need exists, therefore, for a method to produce in high yield, a protein molecule that possesses at least the equivalent, if not enhanced, anticoagulant and other activities, of TFPI and that has reduced glycosylated moieties that would in turn result in reduced immunogenicity of the protein upon administration to a mammal.

SUMMARY OF THE INVENTION

It is, therefore, one of the objects of the present invention to provide a protein that possesses equivalent or enhanced anticoagulant activity, in particular, factor VIIa/TF complex and/or factor Xa inhibitory activity, as compared to fill length TFPI obtained from mammalian cells, yeast cells or bacterial cells.

Another object of the present invention is to produce in high yield, a protein having factor VIIa/TF complex and/or factor Xa inhibitory activity.

Another object of the present invention is to provide a protein having the activity of TFPI, TFPI-2, or both of which target cell surfaces as well or better than TFPI or TFPI-2.

It is further one of the objects of the present invention to provide a protein that has reduced glycosylated moieties as compared to the variants or full length TFPI described in Petersen et al, ibid.

DETAILED DESCRIPTION OF THE INVENTION

Figure 1:
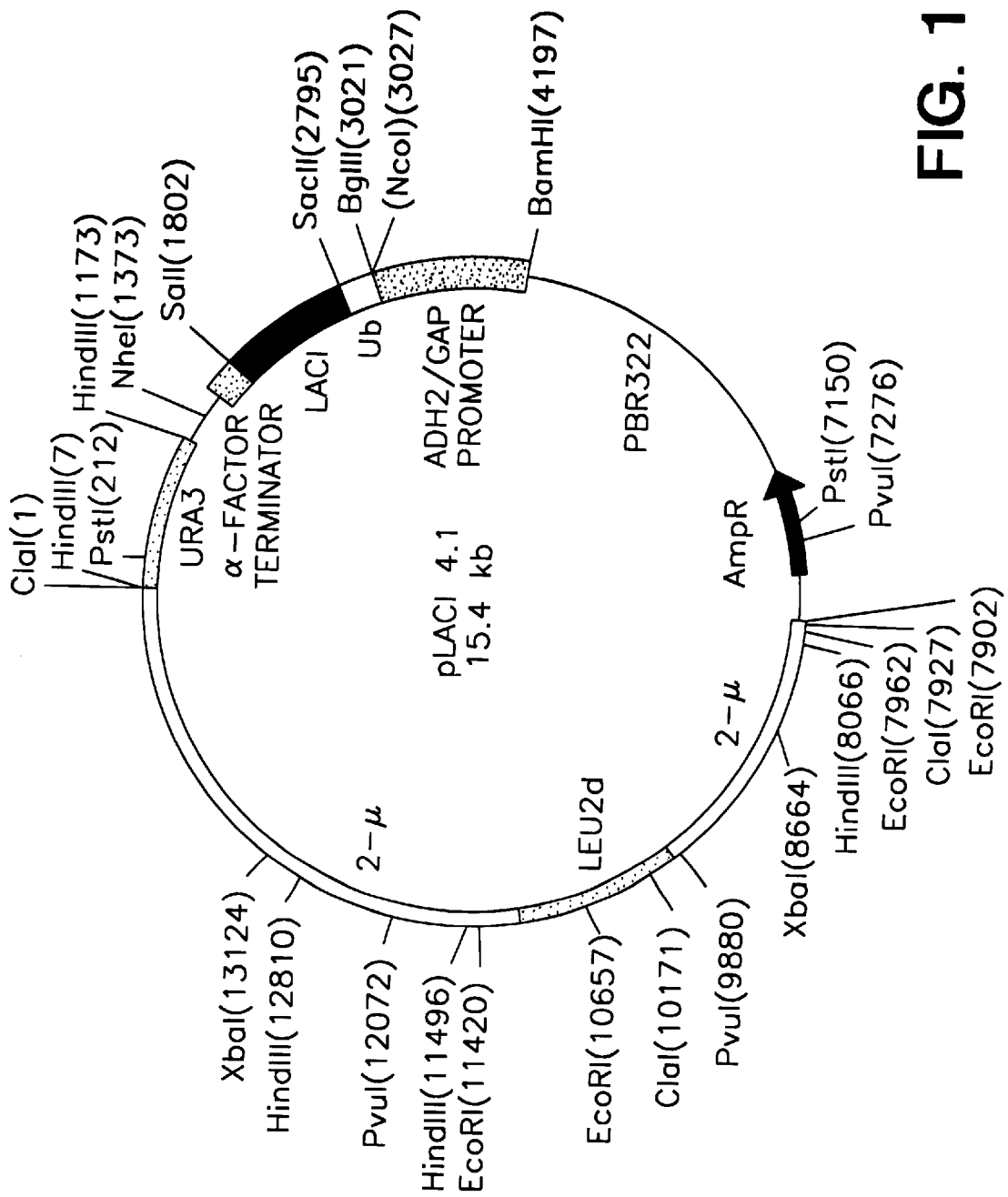
FIG. 1 depicts a schematic of a replicable cloning vehicle (designated pLACI 4.1) including a DNA sequence coding for the TFPI protein.

As used herein, the term "TFPI" refers to the coagulation inhibitor Tissue Factor Pathway Inhibitor, also known as Lipoprotein Associated Coagulation Inhibitor (LACI), Tissue Factor Inhibitor (TFI) and Extrinsic Pathway Inhibitor (EPI). The nucleotide sequence encoding TFPI and the predicted amino acid sequence of TFPI have been disclosed in U.S. Pat. No. 4,966,852, which is herein incorporated by reference.

As used herein, the term "TFPI-2" refers to a coagulation inhibitor, the nucleotide sequence and predicted amino acid sequence of which have been reported by Sprecher et al, *Proc. Nat. Acad. Sci. USA* (1994) 91:3353–3357. The disclosure of Sprecher et al is herein incorporated by reference.

As used herein, the term "factor VIIa/TF/Xa binding protein" refers to proteins capable of binding to the factor VIIa/TF complex thereby inhibiting the function of the complex and further capable of binding factor Xa thereby inhibiting its function. The factor VIIa/TF/Xa binding proteins contain one or more Kunitz-type domains derived from TFPI (or muteins thereof) and one or more Kunitz-type domains from derived TFPI-2 (or muteins thereof).

As used herein, the term "first Kunitz-type domain" refers to amino acids

```
Cys Ala Phe Lys Ala Asp Asp Gly Pro Cys Lys Ala Ile Met Lys Arg    [SEQ ID NO: 1]

Phe Phe Phe Asn Ile Phe Thr Arg Gln Cys Glu Glu Phe Ile Tyr Gly

Gly Cys Glu Gly Asn Gln Asn Arg Phe Glu Ser Leu Glu Glu Cys Lys

Lys Met Cys
``` of TFPI and the amino acid sequence

```
Cys Leu Leu Pro Leu Asp Tyr Gly Pro Cys Arg Ala Leu Leu Leu Arg    [SEQ ID NO: 2]

Tyr Tyr Tyr Asp Arg Tyr Thr Gln Ser Cys Arg Gln Phe Leu Tyr Gly

Gly Cys Glu Gly Asn Ala Asn Asn Phe Tyr Thr Trp Glu Ala Cys Asp

Asp Ala Cys
``` of TFPI-2; the term "second Kunitz-type domain" refers to amino acids

```
Cys Phe Leu Glu Glu Asp Pro Gly Ile Cys Arg Gly Tyr Ile Thr Arg    [SEQ ID NO: 3]
Tyr Phe Tyr Asn Asn Gln Thr Lys Gln Cys Glu Arg Phe Lys Tyr Gly
Gly Cys Leu Gly Asn Met Asn Asn Phe Glu Thr Leu Glu Glu Cys Lys
Asn Ile Cys
``` of TFPI and amino acids

```
Cys Arg Leu Gln Val Ser Val Asp Asp Gln Cys Glu Gly Ser Thr Glu    [SEQ ID NO: 4]
Lys Tyr Phe Phe Asn Leu Ser Ser Met Thr Cys Glu Lys Phe Phe Ser
Gly Gly Cys His Arg Asn Arg Ile Glu Asn Arg Phe Pro Asp Glu Ala
Thr Cys Met Gly Phe Cys
``` of TFPI-2; and the term "third Kunitz-type domain" refers to amino acids

```
Cys Leu Thr Pro Ala Asp Arg Gly Leu Cys Arg Ala Asn Glu Asn Arg    [SEQ ID NO: 5]
Phe Tyr Tyr Asn Ser Val Ile Gly Lys Cys Arg Pro Phe Lys Tyr Ser
Gly Cys Gly Gly Asn Glu Asn Asn Phe Thr Ser Lys Gln Glu Cys Leu
Arg Ala Cys
``` of TFPI and amino acids

```
Cys Tyr Ser Pry Lys Asp Glu Gly Leu Cys Ser AXa Asn Val Thr Arg    [SEQ ID NO: 6]
Tyr Tyr Phe Asn Pro Arq Tyr Arg Thr Cys Asp Ala Phe Thr Tyr Thr
Gly Cys Gly Gly Asn Asp Asn Asn Phe Val Ser Arq Glu Asp Cys Lys
Arg Ala Cys
``` of TFPI-2.

As used herein, the term "C-terminal tail" refers to the amino acid sequences which are carboxy-terminal to the third Kunitz-type domain of TFPI or of TFPI-2, i.e.,

```
Lys Lys Gly Phe Ile Gln Arg Ile Ser Lys Gly Gly Leu Ile Lys Thr    [SEQ ID NO: 7]
Lys Arq Lys Arg Lys Lys Gln Arq Val Lys Ile Ala Tyr Glu Glu Ile
Phe Val Lys Asn Met
``` for TFPI and

```
Ala Lys Ala Leu Lys Lys Lys Lys Met Pro Lys Leu Arg Phe Ala    [SEQ ID NO: 8]
Ser Arg Ile Arg Lys Ile Arg Lys Lys Gln Phe
``` for TFPI-2. These sequences are highly basic and may be involved in cell surface localization by glycosaminoglycan (including heparin) or phospholipid binding. Further description and explanation of Kunitz-type domains 1, 2 and 3 and the $P_1$-reactive site for each domain may be found in Girard et al, *Nature,* 338:518–520 (1989).

As used herein, the term "$P_1$-reactive site" refers to the active site cleft of a Kunitz-type domain. Alteration of the amino acid residue present in the $P_1$ position can profoundly alter the binding, and therefore the inhibitory effect, of the Kunitz-type domain to its target protease.

As used herein, the term "chimeric protein" refers to a polypeptide consisting of one or more domains from different proteins or mutations within a single protein giving the characteristics of another protein. For example, a chimeric protein as used herein would include a factor VIIa/TF/Xa binding protein containing SEQ ID NO: 2 and SEQ ID NO: 1.

As used herein, the term "mutein" refers to a normal or wild-type sequence in which 1–5 amino acid substitutions have been made. For example, a mutein in Kunitz-type domain 1 of TFPI [SEQ ID NO: 1] may be made in the $P_1$ position by changing a lysine residue to an arginine residue. This substitution has the effect of altering the properties of Kunitz-type domain 1 of TFPI, including affinity for factor VIIa/TF complex, to those of Kunitz-type domain 1 of TFPI-2.

As used herein, the term "pharmaceutically acceptable carrier" refers to a medium which does not interfere with the effectiveness of the biological activity of the active ingredient and which is not toxic to the hosts to which it is administered.

As used herein, the term "pharmacologically effective amount" refers to the amount of protein administered to the host that results in reduction of morbidity and mortality resulting from the condition being treated. Conditions that may be treated include sepsis, septic shock and thrombosis disorders, including thrombosis during and after microsurgery and thrombosis from abrupt reclosure after angioplasty. The exact amount administered depends on condition, severity, subject etc., but may be determined by routine methods. The term "pharmacologically effective amount" also refers to the amount of protein administered to the host that prevents morbidity and mortality resulting associated with a condition. Conditions that may be prevented include sepsis, septic shock and thrombosis disorders, including thrombosis during and after microsurgery and thrombosis from abrupt reclosure after angioplasty. The exact amount administered depends on condition, severity, subject etc., but may be determined by routine methods.

Factor VIIa/TF/Xa binding proteins of the invention include muteins of TFPI and TFPI-2, the muteins having single or multiple amino acid substitutions. Muteins within the scope of this definition include: (a) TFPI or TFPI-2 muteins having 1–5 conservative amino acid substitutions that do not substantially change the conformation of the molecule; (b) TFPI or TFPI-2 muteins with amino acid substitutions that eliminate one or more of the three sites for N-linked glycosylation; (c) TFPI muteins having 1–5 amino acid substitutions that change a residue of TFPI to a corresponding residue of TFPI-2; (d) TFPI-2 muteins having 1–5 amino acid substitutions that change a residue of TFPI-2 to a corresponding residue of TFPI; (e) TFPI or TFPI-2 muteins with amino acid substitutions in $P_1$ reactive sites in one or more Kunitz-type domains; and (f) TFPI or TFPI-2 muteins with amino acid substitutions at positions within 5 amino acids of the $P_1$ reactive sites in one or more Kunitz-type domains. In a preferred embodiment, the lysine residue in the $P_1$-reactive site of the first Kunitz-type domain of TFPI [SEQ ID NO: 1] is replaced with arginine. The mutein has the following sequence:

```
Asp Ser Glu Glu Asp Glu Glu His Thr Ile Ile Thr Asp Thr Glu Leu    [SEQ ID NO: 9].

Pro Pro Leu Lys Leu Met His Ser Phe Cys Ala Phe Lys Ala Asp Asp

Gly Pro Cys Arg Ala Ile Met Lys Arg Phe Phe Asn Ile Phe Thr

Arg Gln Cys Glu Glu Phe Ile Tyr Gly Gly Cys Glu Gly Asn Gln Asn

Arg Phe Glu Ser Leu Glu Glu Cys Lys Lys Met Cys Thr Arg Asp Asn

Ala Asn Arg Ile Ile Lys Thr Thr Leu Gln Gln Glu Lys Pro Asp Phe

Cys Phe Leu Glu GIu Asp Pro Gly Ile Cys Arg Gly Tyr Ile Thr Arg

Tyr Phe Tyr Asn Asn Gln Thr Lys Gln cys Glu Arg Phe Lys Tyr Gly

Gly Cys Leu Gly Asn Met Asn Asn Phe Glu Thr Leu Glu Glu Cys Lys

Asn Ile Cys Glu Asp Gly Pro Asn Gly Phe Gln Val Asp Asn Tyr Gly

Thr Gln Leu Asn Ala Val Asn Asn Ser Leu Thr Pro Gln Ser Thr Lys

Val Pro Ser Leu Phe Glu Phe His Gly Pro Ser Trp Cys Leu Thr Pro

Ala Asp Arg Gly Leu Cys Arg Ala Asn Glu Asn Arg Phe Tyr Tyr Asn

Ser Val Ile Gly Lys Cys Arg Pro Phe Lys Tyr Ser Gly Cys Gly Gly

Asn Glu Asn Asn Phe Thr Ser Lys Gln Glu Cys Leu Arg Ala Cys Lys

Lys Gly Phe Ile Gln Arg Ile Ser Lys Gly Gly Leu Ile Lys Thr Lys

Arg Lys Arg Lys Lys Gln Arg Val Lys Ile Ala Tyr Glu Glu Ile Phe

Val Lys Asn Met.
```

Muteins of TFPI and TFPI-2 containing one or more amino acid substitutions may be prepared by appropriate mutagenesis of the sequence of a recombinant cloning vehicle encoding TFPI or TFPI-2, using techniques known to those skilled in the art. Techniques for mutagenesis include, without limitation, site specific mutagenesis. Site specific mutagenesis can be carried out using any number of procedures known in the art. These techniques are described by Smith, *Annual Review of Genetics,* 19:423 (1985), and modifications of some of the techniques are described in *Methods in Enzymology,* 154, part E, (eds.) Wu and Grossman (1987), chapters 17, 18, 19, and 20. A preferred procedure when using site specific mutagenesis is a modification of the Gapped Duplex site directed mutagenesis method. The general procedure is described by Kramer, et al., in chapter 17 of the Methods in Enzymology, above. Another technique for generating point mutations in a nucleic acid sequence is the use of PCR techniques, including overlapping PCR, as described in PCR PROTOCOLS: A GUIDE TO METHODS AND APPLICATIONS, (eds.) Innis, Gelfand, Sninsky and White (Academic Press, 1990).

The muteins of TFPI and TFPI-2 may also be truncated at the end of the second Kunitz-type domain. Such truncated molecules retain the ability to bind factor VIIa/TF complex and Xa yet can be expressed at higher levels in such organisms as yeast. The truncated TFPI and TFPI-2 muteins will likely lead to enhanced recovery of a product containing correctly folded Kunitz-type domains due to the removal of six cysteine residues in the third Kunitz-type domain. The truncated muteins may also have the tail sequence of TFPI or of TFPI-2 attached at the carboxy-terminal end to give the mutein cell surface-binding ability, preferably by binding to glycosaminoglycans (including heparin) or phospholipid at the cell surface.

Chimeric proteins capable of binding factor VIIa/TF and factor $X_a$ and containing various portions of TFPI or TFPI-2 are also within the scope of the invention. One class of proteins within the scope of the invention can be represented by the following generic formula:

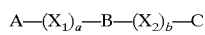

$$A\text{---}(X_1)_a\text{---}B\text{---}(X_2)_b\text{---}C$$

wherein A and C are optional flanking peptides, the flanking peptides independently containing 1–100 amino acids;

wherein B is an optional spacer peptide, the spacer peptide containing 1–25 amino acids;

wherein each $X_1$ is ---D---$K_1$---E---
  where D, E are peptides of 1–25 amino acids,
  where $K_1$ is independently Kunitz-type domain 1 from TFPI or TFPI-2 [SEQ ID NO: 1 or SEQ ID NO: 2] or a mutein of the aforementioned Kunitz-type domains;

wherein each $X_2$ is ---F---$K_2$---G---
  where F, G are peptides of 1–25 amino acids,
  where $K_2$ is independently Kunitz-type domain 2 from TFPI or TFPI-2 [SEQ ID NO: 3 or SEQ ID NO: 4] or a mutein of the aforementioned Kunitz-type domains;

wherein a, b are integers from 0–6; and wherein the molecule is not native TFPI or TFPI-2.

A, B, C, D, E, F, G may independently comprise portions of native TFPI or TFPI-2 sequences. For example, B, D, E, F, and G may independently comprise peptide sequences between Kunitz-type domains 1 and 2 of TFPI or TFPI-2, or peptide sequences between Kunitz-type domains 2 and 3 of TFPI and TFPI-2. The flanking peptides A and C may also have cell surface localization 10 properties and may be the C-terminal tail sequence from TFPI or TFPI-2 [SEQ ID NO: 7 or SEQ ID NO: 8]. Alternatively, other cell surface localizing peptide sequences may be used. These sequences preferably have glycosaminoglycan binding ability and, most preferably, bind heparin. Such peptide sequences may be derived from proteins having heparin binding, activity including, but not limited to, the following: protease nexin-1, protease nexin-2, antithrombin III, protein C inhibitor, platelet factor 4, heparin cofactor II, ghilanten-related inhibitors, and bovine pancreatic trypsin inhibitor. Appropriate portions of these proteins (i.e. those with glycosaminoglycan binding activity) may be attached in the A or C position (or both).

In the case of TFPI, the appropriate portion may be the C-terminal tail [SEQ ID NO: 7] or Lys Thr Lys Arg Lys Arg Lys Lys Gln Arg Val Lys Ile Ala Tyr Glu   [SEQ ID NO: 10].
Glu Ile Phe Val Lys Asn Met.

In the case of TFPI-2, the appropriate portion may be the C-terminal tail [SEQ ID NO: 8] or Lys Lys Lys Lys Lys Met Pro Lys Leu Arg Phe Ala Ser Arg Ile Arg   [SEQ ID NO: 11].
Lys Ile Arg Lys Lys Gln Phe.

In the case of antithrombin III, the appropriate portion may be

Ala Lys Leu Asn Cys Arg Leu Tyr Arg Lys Ala Asn Lys Ser Ser Lys   [SEQ ID NO: 12].
Leu.

The appropriate portion of antithrombin III may also be

```
Thr Ser Asp Gln Ile His Phe Phe [SEQ ID NO: 13].
                    Phe Ala Lys Leu Asn Cys Arg.
```

In the case of protein C inhibitor, the appropriate portion may be:

```
Ser Glu Lys Thr Leu Arg Lys Trp [SEQ ID NO: 14].
    Leu Lys Met Phe Lys Lys Arg Glu Leu Glu Tyr.
```

The appropriate portion of protein C inhibitor may be:

```
His Arg His His Pro Arg Glu Met [SEQ ID NO: 15].
                    Lys Lys Arg Val Glu Asp Leu.
```

In the case of heparin cofactor II, the appropriate portion may be

```
Phe Arg Lys Leu Thr His Arg Leu [SEQ ID NO: 16].
            Phe Arg Arg Asn Phe Gly Tyr Thr Leu Arg.
```

In the case of platelet factor 4, the appropriate portion may be

```
Leu Tyr Lys Lys Ile Leu Lys Lys [SEQ ID NO: 17].
                                Leu Leu Glu Ala.
```

In the case of ghilanten-related inhibitors, the appropriate portion may be

```
Asn Gly Leu Lys Arg Asp Lys Leu [SEQ ID NO: 18].
Gly Cys Glu Tyr Cys Glu Cys Arg Pro Lys Arg Lys
                        Leu Ile Pro Arg Leu Ser.
```

In a preferred embodiment, a factor VIIa/TF/$X_a$ binding protein contains the first Kunitz-type domain [SEQ ID NO: 2], including the amino-terminal sequence, of TFPI-2, the second Kunitz-type domain of TFPI [SEQ ID NO: 3], the third Kunitz-type domain of TFPI [SEQ ID NO: 5] and/or the TFPI C terminal tail sequence[SEQ ID NO: 7]. One skilled in the art will appreciate that this molecule is but one of numerous species that may be produced and that various portions of the peptide sequences linking the Kunitz-type domains from TFPI or from TFPI-2 may be included in the molecule.

Also within the scope of the invention are factor VIIa/TF/$X_a$ binding proteins containing two or more of the same Kunitz-type domain from TFPI or from TFPI-2. For example, factor VIIa/TF/$X_a$ binding proteins comprising two or more iterations of the first Kunitz-type domain of TFPI-2 [SEQ ID NO: 2] may prepared. Such molecules may be particularly useful for increased inhibition of factor VIIa/TF complex. Factor VIIa/TF/$X_a$ binding proteins containing two or more iterations of the second Kunitz-type domain of TFPI [SEQ ID NO: 3] may also be prepared. Such molecules may be particularly useful for the increased inhibition of factor $X_a$ by the protein. A preferred factor VIIa/TF/Xa binding protein containing more than one iteration of the same Kunitz-type domain is represented by the formula:

$$A-[X_1-B-X_2]_c-C$$

wherein A and C are optional flanking peptides, the flanking peptides independently containing 1–100 amino acids;
wherein B is an optional spacer peptide, the spacer peptide containing 1–25 amino acids;
wherein each $X_1$ is —D—$K_1$—E—
where D, E are peptides of 1–25 amino acids,
where $K_1$ is Kunitz-type domain 1 from TFPI or TFPI-2 [SEQ ID NO: 1 or SEQ ID NO: 2] or a mutein of the aforementioned Kunitz-type domains;
wherein each $X_2$ is —F—$K_2$—G—
where F, G are peptides of 1–25 amino acids,
where $K_2$ is Kunitz-type domain 2 from TFPI or TFPI-2 [SEQ ID NO: 3 or SEQ ID NO: 4] or a mutein of the aforementioned Kunitz-type domains;
wherein c is an integer from 1–10.

A, B, C, D, E, F, and ,G may also have the same sequences disclosed above in reference to the generic structure. The factor VIIa/TF/Xa binding protein may be one in which $K_1$ and $K_2$ are SEQ ID NO: 2 and SEQ ID NO: 3.

One skilled in the art of DNA cloning and in possession of the DNA encoding TFPI and TFPI-2 is able to prepare suitable DNA molecules for production of such chimeric proteins using known cloning procedures (e.g. restriction enzyme digestion of TFPI and TFPI-2 encoding DNA, exonuclease digestion, ligation, and other appropriate procedures outlined in any of the following: Sambrook, et al., MOLECULAR CLONING: A LABORATORY MANUAL 2nd ed. (Cold Spring Harbor Laboratory Press, 1989); DNA CLONING, Vol. I and II, D. N. Glover ed. (IRL Press, 1985); OLIGONUCLEOTIDE SYNTHESIS, M. J. Gait ed. (IRL-Press, 1984); NUCLEIC ACID HYBRIDIZATION, B. D. Hames & S. J. Higgins eds. (IRL Press, 1984); TRANSCRIPTION AND TRANSLATION, B. D. Hames & S. J. Higgins eds., (IRL Press, 1984); ANIMAL CELL CULTURE, R. I. Freshney ed. (IRL Press, 1986); IMMOBILIZED CELLS AND ENZYMES, K. Mosbach (IRL Press, 1986); B. Perbal, A PRACTICAL GUIDE TO MOLECULAR CLONING, Wiley (1984); the series, METHODS IN ENZYMOLOGY, Academic Press, Inc.; GENE TRANSFER VECTORS FOR IAN CELLS, J. H. Miller and M. P. Calos eds. (Cold Spring Harbor Laboratory, 1987); METHODS IN ENZYMOLOGY, Vol. 154 and 155, Wu and Grossman, eds., and Wu, ed., respectively (Academic Press, 1987), IMMUNOCHEMICAL METHODS IN CELL AND MOLECULAR BIOLOGY, R. J. Mayer and J. H. Walker, eds. (Academic Press London, Harcourt Brace U.S., 1987), PROTEIN PURIFICATION: PRINCIPLES AND PRACTICE, 2nd ed. (Springer-Verlag, N.Y. (1987), and HANDBOOK OF EXPERIMENTAL IMMUNOLOGY, Vol. I–IV, D. M. Weir et al., (Blackwell Scientific Publications, 1986); Kitts et al., *Biotechniques* 14:810–817 (1993); Munemitsu et al., *Mol. Cell. Biol.* 10:5977–5982 (1990). Alternatively, the entire sequence or portions of nucleic acid sequences encoding proteins described above may be prepared by synthetic methods (e.g. using DNA synthesis machines). Finally, a preferred method of preparing nucleic acid molecules encoding the described chimeric proteins is by use of PCR techniques as described in Innis et al, supra.

The proteins described above may be prepared using any suitable expression system including, without limitation, the following expression systems: mammalian tissue culture, insect cell culture, bacterial cell culture and yeast cell culture. Mammalian expression systems are known in the art. Sambrook et al. (1989) "Expression of Cloned Genes in Mammalian Cells." In *Molecular Cloning: A Laboratory Manual*, 2nd ed. Mammalian cell lines available as hosts for expression are known in the art and include many immortalized cell lines available from the American Type Culture Collection (ATCC). TFPI has been isolated from human plasma and from human tissue culture cells including HepG2, Chang liver and SK hepatoma cells. Recombinant TFPI has been expressed in mouse C127 cells, baby hamster kidney cells, Chinese hamster ovary cells and human SK hepatoma cells.

The proteins of the invention may also be produced in insect cells using a vector containing baculovirus sequences. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, Texas Agricultural Experiment Station Bulletin No. 1555 (1987) hereinafter "Summers and Smith"). Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 base pairs downstream from the ATT; see Luckow and Summers, Virology (1989) 17:31. Methods for introducing heterologous DNA into the desired site in the baculovirus virus are known in the art. (See Summers and Smith supra; Ju et al. (1987); Smith et al, *Mol. Cell. Biol.* (1983) 3:2156, and Luckow and Summers (1989)). For example, the insertion can be into a gene such as the polyhedrin gene, by homologous double crossover recombination; insertion can also be into a restriction enzyme site engineered into the desired baculovirus gene. Miller et al. *Bioessays* 4:91 (1989). The DNA sequence, when cloned in place of the polyhedrin gene in the expression vector, is flanked both 5' and 3' by polyhedrin-specific sequences and is positioned downstream of the polyhedrin promoter.

Recombinant baculovirus expression vectors have been developed for infection into several insect cells. For example, recombinant baculoviruses have been developed for, inter alia: *Aedes aegypti, Bombyx mori, Drosophila melanogaster, Spodoptera frugiperda,* and *Trichoplusia ni* (PCT Pub. No. WO 89/046699; Carbonell et al., *J. Virol.* 56:153 (1985); Wright *Nature* 321:718 (1986); Smith et al., *Mol. Cell. Biol.* 3:2156 (1983); and see generally, Fraser, et al. *Cell. Dev. Biol.* 25:225 (1989). Cells and cell culture media are commercially available for both direct and fusion expression of heterologous polypeptides in a baculovirus/ expression system; cell culture technology is generally known to those skilled in the art. See, e.g., Summers and Smith supra. The modified insect cells may then be grown in an appropriate nutrient medium, which allows for stable maintenance of the plasmid(s) present in the modified insect host. A presently preferred media is described in EPO 380 495.

Numerous bacterial expression techniques are known in the art. Sambrook et al. (1989) "Expression of cloned genes in *Escherichia coli.*" In Molecular Cloning: A Laboratory Manual. Expression and transformation vectors, either extra-chromosomal replicons or integrating vectors, have been developed for transformation into many bacteria. For example, expression vectors have been developed for, inter alia, the following bacteria: *Bacillus subtilis* (Palva et al. (1982) Proc. Natl. Acad. Sci. USA 79:5582; EPO 036 259 and 063 953; PCT WO 84/04541), *E. coli* (Shimatake et al. (1981) Nature 292:128; Amann et al. (1985) Gene 40:183; Studier et al. (1986) J. Mol. Biol. 189:113; EPO Publ. Nos. 036 776, 136 829 and 136 907), *Streptococcus cremoris* (Powell et al. (1988) Appl. Environ. Microbiol. 54:655); *Streptococcus lividans* (Powell et al. (1988) Appl. Environ. Microbiol. 54:655), *Sireptomyces lividans* (U.S. Pat. No. 4,745,056).

The DNA encoding the protein of the present invention may be joined to a signal peptide for export or secretion of the mature protein to the periplasmic space of bacteria, using techniques that are conventional in the art. Moreover, transcription and translation can further be optimized in a bacterial expression system by varying the spacing between the DNA to be expressed and the sequences encoding the promoter and ribosome binding site.

Yeast expression systems are also known in the art. Fusion proteins provide one means for expression of the proteins of the invention in yeast systems. Usually, a DNA sequence encoding the N-terminal portion of an endogenous yeast protein, or other stable protein, is fused to the 5' end of a heterologous coding sequence. Upon expression, this construct will provide a fusion of the two amino acid sequences. The DNA sequence at the junction of the two amino acid sequences may or may not encode a cleavable site. See e.g., EPO 196 056. A preferred fusion protein is a ubiquitin fusion protein. Such a fusion protein is made with the ubiquitin region that preferably retains a site for a processing enzyme, which allows a ubiquitin-specific processing protease to cleave the ubiquitin from the foreign protein. Through this method, therefore, foreign protein with an authentic amino terminus can be isolated from within the yeast cell. Production of ubiquitin fusion proteins is described in co-pending U.S. patent application Ser. Nos. 07/806,813 and 07/957, 627. This method is reviewed in Barr et al, in RECOMBINANT SYSTEMS IN PROTEIN EXPRESSION (Elsevier Science Publishers B.V., 1991), pp. 37–46.

Alternatively, foreign proteins can be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP 012 873; JPO 62,096,086), the α-factor gene (U.S. Pat. Nos. 4,588,684 and 4,870,008; EP 116,201) and truncated versions of the α-factor gene as described in EP 324 274 and co-pending U.S. patent application Ser. No. 07/864,206. Alternatively, leaders of non-yeast origin, such as an interferon leader, exist that also provide for secretion in yeast (EP 060 057). Preferably, the α-factor gene is used in nucleic acid constructs designed for secretion of the proteins of the invention.

Another useful class of secretion leaders are those that employ a fragment of the yeast α-factor gene, which contains both a "pre" signal sequence, and a "pro" region. The types of α-factor fragments that can be employed include the full-length pre-pro a factor leader (about 83 amino acid residues) as well as truncated α-factor leaders (usually about 25 to about 50 amino acid residues) (U.S. Pat. Nos. 4,546, 083 and 4,870,008; EP 324 274). Additional leaders employing an α-factor leader fragment that provides for secretion include hybrid α-factor leaders made with a presequence of a first yeast, but a pro-region from a second yeast α-factor. (See e.g., PCT WO 89/02463.)

Expression vectors encoding the proteins of the invention are often maintained in a replicon, such as an extrachromosomal element (e.g., plasmid) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 (Botstein et al, Gene 8:17–24 (1979)), pCl/1 (Brake et al, Proc. Natl. Acad. Sci USA 81:4642–4646 (1984)), and YRp17 (Stinchcomb et al, J. Mol. Biol. 158:157 (1982)). In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Either a high or low copy number vector may be selected, depending upon the effect of the vector and the foreign protein on the host. See e.g., Brake et al, supra. For production of the proteins of the invention in a yeast cell wherein the protein is retained within the yeast cell, a plasmid such as pAB24 may be used. Sabin et al, (1989) Bio/Technology 7:705–709. pAB24 contains a GAP/ADH hybrid promoter, containing portions of an ADH promoter capable of directing high levels of expression of the sequences under its control but which also contains GAP regulatory sequences, allowing expression of the same sequence a desired point in the growth of a culture.

Alternatively, the expression constructs can be integrated into the host genome with an integrating vector. Integrating vectors usually contain at least one sequence homologous to a host chromosome that allows the vector to integrate, and preferably contain two homologous sequences flanking the expression construct. Integrations appear to result from recombinations between homologous DNA in the vector and the host chromosome. Orr-Weaver et al, *Meth. Enzymol.* 101:228–245 (1983). An integrating vector may be directed to a specific locus in yeast by selecting the appropriate homologous sequence for inclusion in the vector. See Orr-Weaver et al, supra. One or more expression construct may integrate, possibly affecting levels of recombinant protein produced. Rine et al, *Proc. Natl. Acad. Sci.* USA 80:6750 (1983). The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7 and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions (Butt et al, *Microbiol. Rev.* 51:351 (1987)).

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* (Kurtz, et al, *Mol. Cell. Biol.* 6:142 (1986)), *Candida maltosa* (Kunze, et al, *J. Basic Microbiol.* 25:141 (1985)), *Hanssenula polymorpha* (Gleeson, et al, *J. Gen. Microbiol.* 132:3459 (1986); Roggenkamp et al, *Mol. Gen. Genet.* 202:302 (1986)), *Khuyveromyces fragilis* (Das, et al, *J. Bacteriol.* 158:1165 (1984)), *Khuyveromyces lactis* (De Louvencourt et al, *J. Bacteriol.* 154:737 (1983); Van den Berg et al, *Bio/Technology* 8:135 (1990)), *Pichia guillerimondi* (Kunze et al, *J. Basic Microbiol.* 25:141 (1985)), *Pichia pastoris* (Cregg, et al, *Mol. Cell. Biol.* 5:3376 (1985); U.S. Pat. Nos. 4,837,148 and 4,929,555), *Saccharomyces cerevisiae* (Hinnen et al, *Proc. Natl. Acad. Sci.* USA 75:1929(1978); Ito et al, *J. Bacteriol.* 153:163 (1983)), *schizosaccharomyces pombe* (Beach and Nurse, *Nature* 300:706 (1981)), and *Yarrowia lipolytica* (Davidow, et al, *Curr. Genet.* 10:380471 (1985) and Gaillardin et al, *Curr. Genet.* 10:49 (1985)).

Transformation procedures that may be used herein to transform yeast cells include electroporation, as described in "Guide to Yeast Genetics and Molecular Biology," Vol 194 METHODS IN ENZYMOLOGY, C. Guthrie and G. R. Fink, (Academic Press 1991). Other procedures include the transformation of spheroplasts or the transformation of alkali cation-treated intact cells. Such procedures are described in, for example, Kurtz et al, *Mol. Cell. Biol.* 6:142 (1986); Kunze et al, *J. Basic Microbiol.* 25:141 (1985), for Candida; Gleeson et al, *J. Gen. Microbiol.* 132:3459 (1986); Roggenkamp et al., *Mol. Gen. Genet.* 202:302, for Hansenula (1 986); Das et al, *J. Bacteriol.* 158:1165 (1984); De Louvencourt et al, *J. Bacteriol.* 154:1165 (1983); Van den Berg et al, *Bio/Technology* 8:135 (1990) for Kluyveromyces; Cregg et al, *Mol. Cell. Biol.* 5:3376 (1985); Kunze et al, *J. Basic Microbiol.* 25:141 (1985); U.S. Pat. Nos. 4,837, 148 and 4,929,555, for Pichia; Hinnen et al, *Proc. Natl. Acad. Sci. USA* 75:1929 (1978); Ito et al, *J. Bacteriol.* 153:163 (1983), for Saccharomyces; Beach and Nurse, *Nature* 300:706 (1981), for Schizosaccharomyces; Davidow et al, *Curr. Genet.* 10:39 (1985); Gaillardin et al, *Curr. Genet.* 10:49 (1985), for Yarrowia.

Yeast cell culture, especially *Saccharomyces cerevisiae*, are preferred for production of the proteins of the invention. In a preferred embodiment, the chimeric protein having the primary amino acid sequence:

```
Asp Ser Glu Glu Asp Glu Glu His Thr Ile Ile Thr Asp Thr Glu Leu   [SEQ ID NO: 19]

Pro Pro Leu Lys Leu Met His Ser Phe Cys Ala Phe Lys Ala Asp Asp

Gly Pro Cys Arg Ala Ile Met Lys Arg Phe Phe Phe Asn Ile Phe Thr

Arg Gln Cys Glu Glu Phe Ile Tyr Gly Gly Cys Glu Gly Asn Gln Asn

Arg Phe Glu Ser Leu Glu Glu Cys Lys Lys Met Cys Thr Arg Asp Asn

Ala Asn Arg Ile Ile Lys Thr Thr Leu Gln Gln Glu Lys Pro Asp Phe
```

-continued

```
Cys Phe Leu Glu Glu Asp Pro Gly Ile Cys Arg Gly Tyr Ile Thr Arg

Tyr Phe Tyr Asn Gln Gln Thr Lys Gln Cys Glu Arg Phe Lys Tyr Gly

Gly Cys Leu Gly Asn Met Asn Asn Phe Glu Thr Leu Glu Glu Cys Lys

Asn Ile Cys Glu Asp Gly Pro Asn Gly Phe Gln Val Asp Asn Tyr Gly

Thr
``` is produced in a yeast cell as a fusion protein with α-factor.

Alternatively, the flanking peptides may contain sequences derived from other protease inhibitors, especially protein inhibitors which act at the cell surface. The protein inhibitor protease nexin 1 (hereinafter, nexin) is but one example. Nexin is known to bind heparin thereby helping to localize nexin on the cell surface. Further, nexin binds to and inhibits factor Xa.

The factor VIIa/TF/$X_a$ binding proteins of the invention may be assayed for activity by a prothrombin time clotting assay or a factor Xa amidolytic assay (Wun et al, *J. Biol. Chem.* 265:16096 (1990)) as set forth in the Examples below.

Formulation and Administration

Factor VIIa/TF/$X_a$ binding proteins of the invention may be administered at a concentration that is therapeutically effective to treat and prevent septic shock. To accomplish this goal, the factor VIIa/TF/$X_a$ binding proteins of the invention are preferably administered intravenously. Methods to accomplish this administration are known to those of ordinary skill in the art.

Before administration to patients, formulants may be added to the factor VIIa/TF/Xa binding proteins of the invention. A liquid formulation may be used. For example, these formulants may include oils, polymers, vitamins, carbohydrates, amino acids, salts, buffers, albumin, surfactants, or bulking agents. Carbohydrates which may be used in the formulation include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. Sugar alcohol is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Further, the use of sulfates should be avoided in preparation of the formulation. Preferably, the concentration is from 0.01 to 0.3 molar. Surfactants that can be added to the formulation are shown in EP Nos. 270,799 and 268,110.

Additionally, the factor VIIa/TF/Xa binding proteins of the invention can be chemically modified by covalent conjugation to a polymer to increase its circulating half-life, for example. Preferred polymers, and methods to attach them to peptides, are shown in U.S. Pat. Nos. 4,766,106, 4,179,337, 4,495,285, and 4,609,546 which are all hereby incorporated by reference in their entireties. Preferred polymers are polyoxyethylated polyols and polyethyleneglycol (PEG). PEG is soluble in water at room temperature and has the general formula: $R(O—CH_2—CH_2)_nO—R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/factor VIIa/TF/Xa of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, *J. Bio. Chem.* 263:15064–15070, and a discussion of POG/protein conjugates is found in U.S. Pat. No. 4,766,106, both of which are hereby incorporated by reference in their entireties.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

Administration to Affected Individuals

Factor VIIa/TF/Xa binding proteins of the invention are useful to treat mammals with sepsis or septic shock. Generally, conditions are characterized by high fever (>38.5° C.) or hypothermia (>35.5° C.), low blood pressure, tachypnea (>20 breaths/minute), tachycardia (>100 beats/ minute), leukocytosis (>15,000 cells/mm³) and throinbocytopenia (<100,000 platelets/mm3). The factor VIIa/TF/Xa binding proteins of the invention are preferably administered as soon as the subject is suspected of being septic; presenting a >20% drop in fibrinogen or appearance of fibrin split products, a rise in the subject's temperature and the diagnosis of leukopenia and hypotension associated with septic shock. As stated above, intravenous administration is preferred. Generally, factor VIIa/TF/Xa binding proteins of the invention are given at a dose between 1 µg/kg and 20 mg/kg, more preferably between 20 µg/kg and 10 mg/kg, most preferably between 1 and 7 mg/kg. Preferably, it is given as a bolus dose, to increase circulating levels by 10–20 fold and for 4–6 hours after the bolus dose. Continuous infusion may also be used after the bolus dose. If so, the factor VIIa/TF/Xa binding proteins of the invention may be infused at a dose between 5 and 20 µg/kg/minute, more preferably between 7 and 15 µg/kg/minute.

The factor VIIa/TF/Xa binding proteins of the invention may be given in combination with other agents which would be effective to treat septic shock. For example, the following may be administered in combination with the factor VIIa/TF/Xa binding proteins of the invention antibiotics that can treat the underlying bacterial infection; monoclonal antibodies that are directed against bacterial cell wall components; monoclonal antibodies and soluble receptors that can complex with cytokines that are involved in the sepsis pathway, including, but not limited to tumor necrosis factor (TNF), Interleukin-1, γ-interferon and interleukin-8; and generally any agent or protein that can interact with cytokines or complement proteins in the sepsis pathway to reduce their effects and to attenuate sepsis or septic shock.

Antibiotics useful in the present invention include those in the general category of: beta-lactam rings (penicillin), amino sugars in glycosidic linkage (amino glycosides), macrocyclic lactone rings (macrolides), polycyclic derivatives of napthacenecarboxamide (tetracyclines), nitrobenzene derivatives of dichloroacetic acid, peptides (bacitracin, gramicidin, and polymyxin), large rings with a conjugated double bond system (polyenes), sulfa drugs derived from sulfanilamide (sulfonamides), 5-nitro-2-furanyl groups (nitrofurans), quinolone carboxylic acids (nalidixic acid), and many others. Other antibiotics and more versions of the above specific antibiotics may be found in Encyclopedia of Chemical Technology, 3rd Edition, Kirk-Othymer (ed.), Vol. 2, pages 782–1036 (1978) and Vol. 3, pages 1–78, Zinsser, *Microbiology*, 17th Edition W. Joklik et al (Eds.) pages 235–277 (1980), or Dorland's Illustrated Medical Dictionary, 27th Edition, W. B. Saunders Company (1988).

Other agents which may be combined with the factor VIIa/TF/Xa binding proteins of the invention include monoclonal antibodies directed to cytokines involved in the sepsis pathway, such as those monoclonal antibodies directed to IL-6 or M-CSF, such as shown in PCT US90/07411; monoclonal antibodies directed to TNF, such as shown in U.S. Pat. No. 4,603,106; inhibitors of proteins that cleave the mature TNF prohormone from the cell in which it was produced, such as shown in PCT US90/03266 and PCT US93/06120; antagonists of IL-1, such as shown in PCT US91/02460; inhibitors of IL-6 cytokine action such as activin, such as shown in PCT US90100321; and receptor based inhibitors of various cytokine such as IL-1. Antibodies to or small molecule inhibitors of complement protein may also be employed.

Generally, the factor VIIa/TF/Xa binding proteins of the invention may be useful for those diseases that occur due to the up-regulation of tissue factor brought on by injury, trauma, endotoxin, TNF, cancer, IL-1 or other agents or conditions.

EXAMPLES

The present invention will now be illustrated by reference to the following examples which set forth particularly advantageous embodiments. However, it should be noted that these embodiments are illustrative and are not to be construed as restricting the invention in any way.

Example 1

The shuttle vector pBS24 is described in Barr et al, EXPRESSION SYSTEMS & PROCESSES FOR rDNA PRODUCTS (American Chemical Society, 1991), pp 51–64). pBS24Ub is a derivative of pBS24.1, and contains an expression cassette flanked by unique Bam HI and Sal I restriction sites, the glucose regulatable ADH2/GAP promoter and a synthetic ubiquitin (Ub) gene. For construction of Ub fusions, a unique Ss/II site is generated in the 3' end of the Ub gene. The presence of the Ss/II site allows in-frame insertion of nucleotide sequences for expression as ubiquitin fusion peptides. Insertion can be accomplished by use of synthetic DNA adapters or PCR methodologies. Methods for using synthetic DNA adapters (linkers) are known in the art. All enzymatic modifications of DNA and protein are done according to the instructions provided by the manufacturer of the enzyme. PCR protocols are described in PCR PROTOCOLS: A GUIDE TO METHODS AND APPLICATIONS, (eds.) Innis, Gelfand, Sninsky and White (Academic Press, 1990). In either case, the 5'-junction sequence will be:

```
    ARG GLY GLY           [SEQ ID NO: 20]

C CGC GGY GGC

G GCG CCA CCG

SstII
``` and the 3' cloning site (Sal I) should be as close as possible to the 3' end of the termination codon.

PCR was used to construct the ubiquitin/TFPI gene fusion in the 15.4 kb plasmid pLACI 4.1 shown in FIG. 1. TFPI encoding nucleic acid was amplified using standard PCR procedures with the primers SEQ ID NO: 21 and SEQ ID NO: 22. SEQ ID NO: 21 hybridizes to the 10 nucleotides at the 5' end of nucleic acid mature encoding TFPI and also contains ubiquitin sequence with the Sst II restriction site. SEQ ED NO: 22 hybridizes to the 15 nucleotides at the 3' end of nucleic acid encoding mature TFPI and also trailing sequence with a Sal I restriction site. The sequences of these primers are as follows:

SEQ ID NO: 21 GCTCCGCGGTGGCGATTCTGAG-GAGGAGATGAAGAAC

SEQ ID NO: 22 TCTGTCGACTCACATATTTTAA-CAAAAATTTCTTCAT

After amplification, the PCR product was digested with Sal I and Ss/t II using conditions specified by the manufacturer of the enzymes. The digested PCR product was then cloned into pBS24Ub, as described above, to produce pLACI 4.1.*S. cerevisiae* strain AB 122 transformed with pLACI4.1 has was deposited with the ATCC on Jul. 19, 1994 and has been given Accession Number 74291.

pLACI 4.1 was used to transform three strains of *Saccharomyces cerevisiae:* VH6 (MAT α, cir°, leu-2-112-3, ura3, FoA, pep4::His3), AB122 (MAT α, cir°, leu2, ura3-52, prb1-1112, pep4-3, prc1-407) and JSC310 (as AB122,+ ADR1 overexpression). Transformants of VH6 produced TFPI at levels of approximately 5% of total protein, transformants of AB122 produced TFPI at levels of approximately 10% of total protein and transformants of JSC310 produced TFPI at levels of approximately 15% of total protein. TFPI expressed according to this method was shown to have biological activity, that is TFPI showed both factor VIIa/TF and factor Xa inhibition.

Example 2

TFPI was expressed as a full length fusion protein with prepro a factor leader. The α-factor/TFPI fusion protein was constructed using pAB125 as an intermediate plasmid. (Chang et al, J. Immunol. 149:548–555 (1992)). pAB125 contains an expression cassette flanked by unique Bam HI and Sal I restriction sites, the glucose regulatable ADH2/GAP promoter and the α-factor prepro leader sequence and processing site. For construction of α-factor fusions, a unique Xba I site is generated in the 3' end of the a factor leader gene sequence. The presence of the Xba I site allows in-frame insertion of nucleotide sequences for expression as a factor fusion peptides. Insertion can be accomplished by use of synthetic DNA adapters or PCR methodologies. In either case, the 5' junction sequence will be

```
LeuAspLysArg        [SEQ ID 23]

TCTAGATAAAAGA

AGATCTATTTTCT

Xba I
``` and the 3' cloning site (Sal I) should be as close as possible to the 3' end of the termination codon.

PCR was used to construct the α-factor/TFPI gene fusion in the 15.4 kb plasmid pLACI2.1. TFPI encoding nucleic acid was amplified using standard PCR procedures with the primers SEQ ID NO: 24 and SEQ ID NO: 22. SEQ ID NO: 24 hybridizes to the 22 nucleotides at the 5' end of nucleic acid encoding mature TFPI and also contains α-factor sequence with the Xba I restriction site as shown above. 22 hybridizes to the 29 nucleotides at the 3' end of nucleic acid encoding mature TFPI and trailing sequence with a Sal I restriction site. The sequence of SEQ ID NO: 24 is as follows:

SEQ ID NO: 24 ATCTCTAGATAAAAGAGATTCT-GAGGAAGATGAAGAAC

After amplification, the PCR product was digested with Sal I and Xba I using conditions specified by the manufacturer of the enzymes. The digested PCR product was then cloned into pAB125 which had been previously digested with Sal I and Xba I. The Bam HI to Sal I fragment of pAB125 containing the α-factor/TFPI fusion protein was isolated and subcloned into pBS24.1 to produce pLACI2.1 pLACI2.1 was used to transform the VH6 and AB122 strains of S. cerevisiae.

Example 3

Truncated TFPI, containing amino acids 1–161 of mature TFPI, was expressed as an α-factor fusion protein for secretion. Preparation of TFPI-encoding sequence was accomplished essentially as in Example 2 using SEQ ID NO: 24 and a second primer, SEQ ID NO: 25, which hybridizes within the TFPI coding sequence. The sequence of SEQ ID NO: 25 is as follows:

SEQ ID NO: 25 TCTGTCGACTCAGGTTCCATAAT-TATCCACCT

Alternatively, truncated TFPI can be expressed as a ubiquitin fusion protein and recovered from within the yeast cell.

In order to prepare the appropriate coding sequence, the LACI4 and LACI2 primers are used to prepare the coding region for subcloning into pBS24-Ub as described above.

Example 4

Yeast shake flask cultures were harvested by centrifugation and the supernatant fluids containing α-factor-TFPI were collected and filtered through 0.8µ membranes. The cells from TFPI cultures were pelleted by centrifugation. Cell lysates from α-factor-TFPI and ubiquitin-TFPI were prepared by disrupting cell pellets in 50 mM Tris pH 7.5, 2 mM EDTA, 50 mM NaCl, 1 mM PMSF by vortexing with glass beads. In some cases, the cell lysates were further fractionated into soluble and insoluble fractions by centrifugation at 12000 g for 10 minutes at 4° C.

Figure 2A:
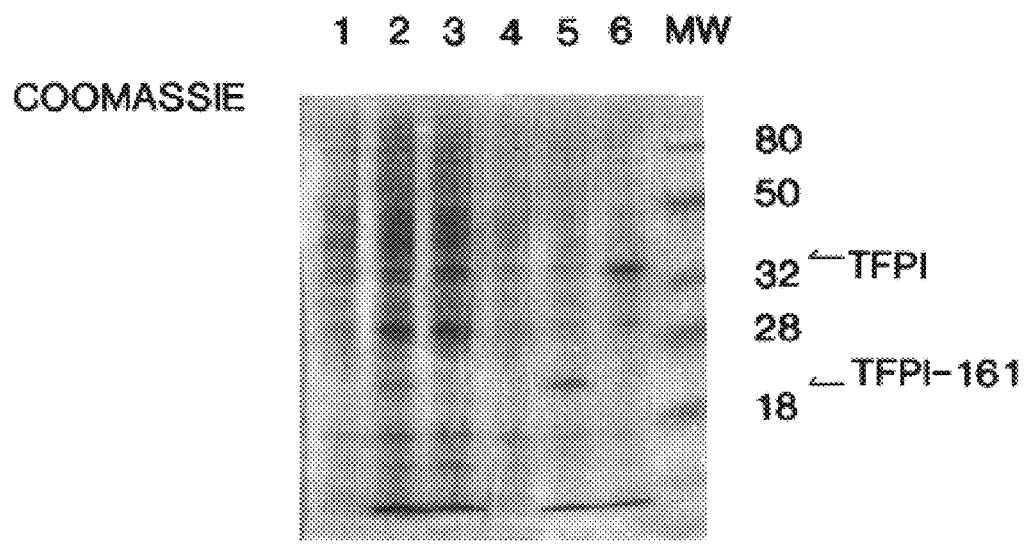
FIG. 2A shows a Coomassie stained gel containing full length and truncated versions of TFPI initially expressed as ubiquitin and α-factor fusions.
Figure 2B:
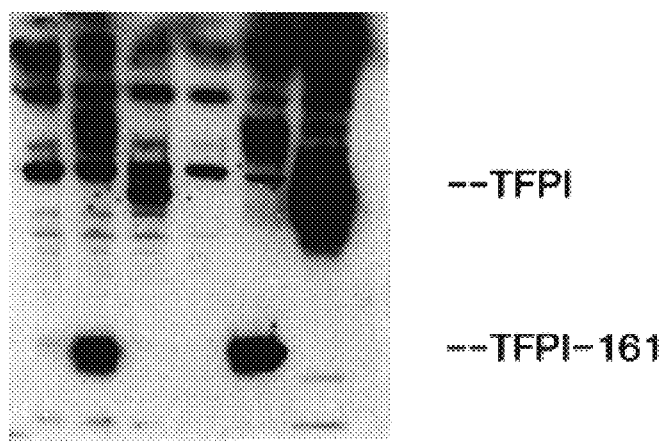
FIG. 2B shows the results of a Western blot of the gel of FIG. 2A with antisera specific for the amino-terminal end of TFPI. For both 2A and 2B, the lanes were loaded as follows: soluble protein isolated from culture medium in which control cells (V2) were grown (Lane 1); soluble protein isolated from yeast cells expressing a LACI fragment (amino acids 1–161) (Lane 2); soluble protein isolated from yeast cells expressing full length LACI (Lane 3), protein isolated from control yeast cells (Lane 4); protein isolated from yeast cells expressing a LACI fragment (amino acids 1–161) (Lane 5); protein isolated from yeast cells expressing full length LACI (Lane 6); and molecular weight markers (Lane 7).

Expression of TFPI was detected by SDS/PAGE followed by Coomassie staining or by Western blotting with a rabbit antiserum raised against the first 15 amino acids of TFPI (NTP sera). Analysis of the soluble and insoluble fractions of cell lysates is shown in FIGS. 2A and 2B. Coomassie-stained gels (top panel) reveal the presence of unique bands Inigrating at ~21 kD in the soluble fraction of α-factor-truncated TFPI (aa 1-161) (Lane 2, FIG. 2A and FIG. 2B) and insoluble fractions of ubiquitin- truncated TFPI (aa 1-161) (Lane 5, FIG. 2A and FIG. 2B) which were verified to represent truncated TFPI by Western blotting (Lanes 2 and 5, FIG. 2B). Full-length TFPI migrating at 35 kD was detectable in the insoluble fraction of ubiquitin-TFPI lysates (Lane 6, FIG. 2A and FIG. 2B) by Coomassie staining and Western blotting and was identified in the soluble fraction of α-factor TFPI lysates by Western blotting. (Lane 3, FIG. 2B). Lanes 1 and 4 of FIGS. 2A and 2B contained negative control proteins isolated as above from non-transformed yeast cell culture.

Figure 3A:
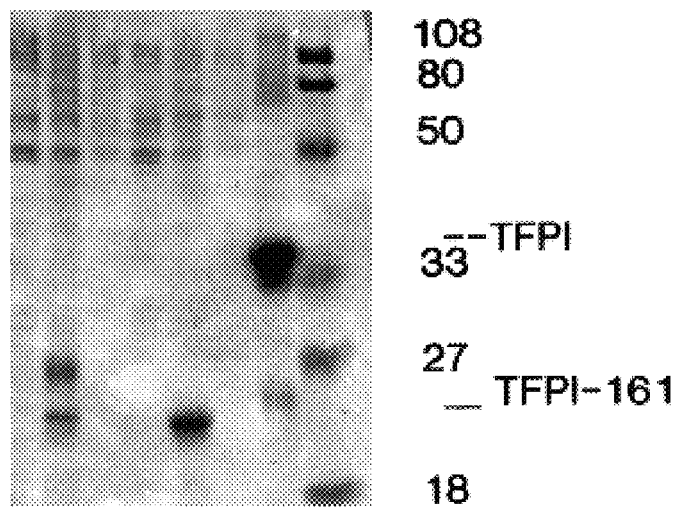
FIG. 3A shows a Coomassie stained gel containing full length and truncated versions of TFPI before and after digestion with N glycanase to remove the sugars.
Figure 3B:
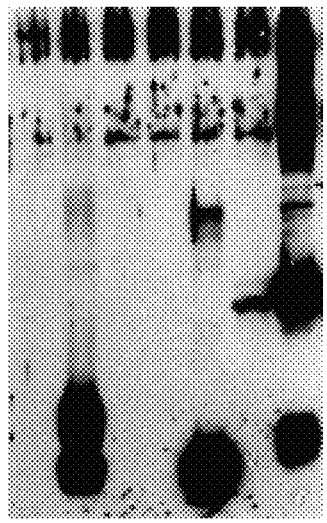
FIG. 3B shows the results of a Western blot of the gel of FIG. 3A with antisera specific for the amino-terminal end of TFPI. The gel was loaded as follows: proteins from V2 control cells (Lane 1); proteins from yeast cells expressing a LACI fragment (amino acids 1–161) (Lane 2); proteins from yeast cells expressing full length LACI (Lane 3); proteins from V2 control cells treated with N-glycanase (Lane 4); proteins from yeast cells expressing a LACI fragment (amino acids 1–161) treated with N-glycanase (Lane 5); proteins from yeast cells expressing full length LACI treated with N-glycanse (Lane 6); LACI standard (Lane 7) and molecular weight markers (Lane 8).

Expression of secreted TFPI was detected by analysis of culture supernates. Biochemical analysis of protein expression included SDS/PAGE followed by Coomassie staining or Western blotting with NTP sera. Since truncated TFPI may be N-glycosylated at one site and full-length TFPI has the potential for modification by N-glycosylation at three sites, the supernatant samples were concentrated five-fold, dialyzed against Tris buffer and deglycosylated with N-glycanase according to the manufacturer's recommendations (Genzyme). As shown in FIG. 3, truncated TFPI was easily detectable by Coomassie staining and by Western blotting as major bands migrating at ~21 and 25 kD (Lane 2, FIG. 3A and FIG. 3B). The 25 kD band was verified as representing glycosylated truncated TFPI by conversion of the doublet to the single 21 kD band following N-glycanase digestion (Lane 5, FIG. 3A and FIG. 3B). While secreted full-length TFPI was not as readily identified prior to N-glycanase treatment (Lane 3, FIG. 3A and FIG. 3B), the 35 kD TFPI band could be observed following deglycosylation (Lane 6, FIG. 3A and FIG. 3B). Lanes 1 and 4 of FIGS. 3A and 3B contained negative control proteins isolated as above from non-transformed yeast cell culture.

Figure 4:
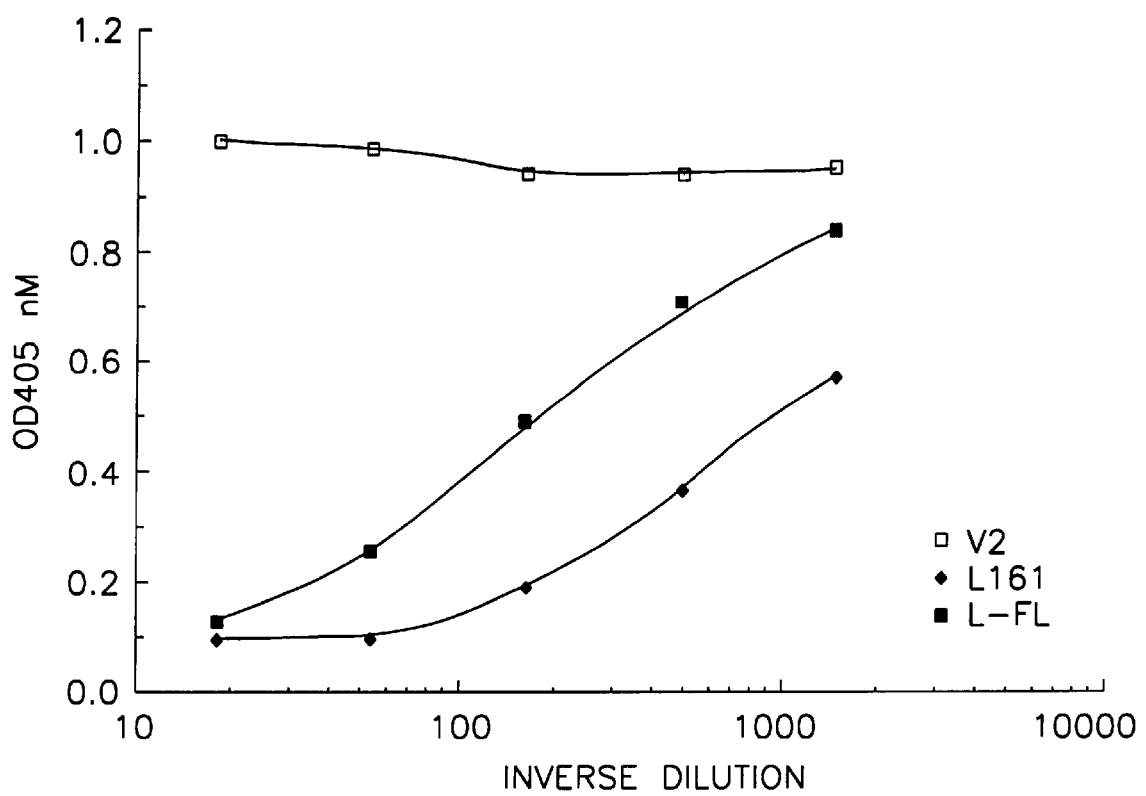
FIG. 4 shows the results of an amidolytic assay performed on truncated and full-length TFPI initially expressed as α-factor fusions and secreted from the yeast cell.

Biological assays were performed using supernatants and soluble fractions of cell lysates of TFPI cultures. A prothrombin time clotting assay (Wun et al, J. Biol. Chem. 265:16096 (1990)) indicated weak TFPI activity in unconcentrated supernatants from cultures secreting truncated TFPI, while the soluble fraction of intracellularly expressed truncated and full-length TFPI exhibited TFPI activity as compared to the intracellular control. A more sensitive assay of TFPI activity, the inhibition of factor Xa activity (Wun et al, ibid) was performed on supernates from cultures producing truncated and full-length TFPI. As shown in FIG. 4, significant Xa inhibitory activity was evident in supernates from cultures secreting truncated TFPI (L161) and full length TFPI (L-FL) as compared to negative control (V2) yeast culture.

Example 5

Potential sites for N-linked glycosylation within TFPI are removed using overlapping PCR as described in Innis et al, supra. As in the previous examples, TFPI-encoding sequences are prepared by PCR, cloned in pAB125 and further subcloned in pBS24. I for expression.

For replacement of the asparagine at position 116 with glutamine, the following overlapping primers are used:

SEQ ID NO: 26 AGGTATTTTTATAACAATCAGA-CAAAACAGTGT

SEQ ID NO: 27 GAAACGTTCACACTGTTTTGTCT-GATTGTTATA

For replacement of the asparagine at position 167 with glutamine, the following overlapping primers are used:

SEQ ID NO: 28 CCAGCTCAATGCTGTGAATAACTC-CCTGACTCCG

SEQ ID NO: 29 CTTGGTTGATTGCGGAGTCAGG-GAGTTATTCACAGC

For replacement of the asparagine at position 227 with glutamine, the following overlapping primers are used:

SEQ ID NO: 30 GGGGGAAATGAAAACAATTTTACT-TCCAAACAA

SEQ ID NO: 31 CCTCAGACATTCTTGTTTGGAAG-TAAAATTGTTTTC

In each case, the LACI1 and LACI3 primers are used to provide the necessary Xba I and Sal I sites for cloning. To introduce more than one mutation, thereby eliminating another potential glycosylation site, sequential rounds of overlapping PCR may be used.

Example 6

In order to produce a mutein of TFPI containing a Lys to Arg substitution in the P1 reactive site of Kunitz-type domain 1, a Bgl II-Sal I fragment from pBS24Ub/TFPI1 was subcloned into pSP72 (commercially available from Promega). A Ava III-Bsp HI fragment was then prepared using the following primers:

SEQ ID NO: 32 CCGATGCATTCATTTTGTGCATTC

SEQ ID NO: 33 CCTCATGATTGCCCGACATGGCC

The second primer contains a single mismatch from the native sequence resulting in the desired Lys to Arg mutation in the resulting fragment. This mutated sequence is then used to replace the Ava III-Bsp HI fragment in the TFPI-encoding sequence previously cloned into pSP72. The resulting plasmid is then digested with Sst II and Sal I and cloned into pBS24-Ub for expression.

Example 7

Constructs encoding chimeric TFPI proteins in which the Kunitz-type domain 1 of TFPI is replaced with the Kunitz-type domain 1 of TFPI-2 were prepared using overlapping PCR. A Sst II-Bsm I restriction fragment, containing Kunitz-type domain 1 of TFPI-2 and part of Kunitz-type domain 2 of TFPI, was generated by overlapping PCR. The primers used were:

SEQ ID NO: 34 GGTCCGCGGTGGTGATGCTGCT-CAGGAGC

SEQ ID NO: 35 GCAATGTTGTTTTTTCTATCCTC-CAGCAAGCAT

These two primers were used to prepare a 93 bp fragment using the TFPI-2 coding sequence as a template. The TFPI-2 coding sequence was cloned using PCR. Primers for cloning were derived from the sequence published in Sprecher et al, *Proc. Nat. Acad. Sci. USA* 91:3353–3357 (1994).

A 54 bp fragment was then prepared using TFPI coding sequence as a template and the following primers:

SEQ ID NO: 36 GGATAGAAAAAAACAACATTG-CAACAAGAAAAGC

SEQ ID NO: 37 GGTTCTTGCATTCTTCCAGTGTCT-CAAAATTG

Overlapping PCR was then performed to join these two fragments using the primers TFOLA and TFOLD. The 126 bp product was then digested with Sst II and Bsm I and exchanged for the equivalent Sst I-Bsm I fragment in pSP72/TFP1. This construct was subsequently digested with Sst II and Sal I and the resulting fragment cloned in pBS24-Ub for expression.

Example 8

Yeast strains are produced containing och1, mnn1 and alg3 mutations resulting in reduction of carbohydrate attached to secreted TFPI molecules of the invention. The genes are cloned using standard PCR techniques based on sequences available to one skilled in the art.

Deletions of 300 bp or more in the OCH1, MNN1 and ALG3 genes are introduced into the coding region of each of these genes. The genes with sequences deleted are then cloned into URA3-based integrating vector. The wild type genes for each of the three are sequentially replaced using the pop-in/pop-out replacement vector as described in Scherer and Davis, *Proc. Nat. Acad. Sci. USA* 76:4951 (1979).

The foregoing discussion and examples only illustrate the present invention, persons of ordinary skill in the art will appreciate that the invention can be implemented in other ways, and the invention is defined solely by reference to the claims. Further, all references, patents and patent applications cited in the foregoing specification are incorporated herein by reference.

We claim:

1. A chimeric protein comprising:
   (a) a Kunitz-type domain 1 of Tissue Factor Pathway Inhibitor-2 (TFPI-2), and
   (b) a Kunitz-type domain 2 of Tissue Factor Pathway Inhibitor (TFPI); or
   (c) a Kunitz-type domain 1 of TFPI, and
   (d) a Kunitz-type domain 2 of TFPI-2
   said chimeric protein lacking sites for N-glycosylation.

2. The chimeric protein of claim 1, wherein said chimeric protein is represented by the generic structure:

$$A-(X_1)_a-B-(X_2)_b-C$$

wherein A and C are independently optional flanking peptides, the flanking peptides containing 0–100 amino acids;
   wherein B is an optional spacer peptide, the spacer peptide containing 0–25 amino acids;
   wherein each $X_1$ is $-D-K_1-E-$
   where D, E are independently polypeptides of 0–25 amino acids,
   where $K_1$ comprises TFPI Kunitz-type domain 1 or TFPI-2 Kunitz-type domain 1;
   wherein each $X_2$ is $-F-K_2-G-$
   where F, G are independently polypeptides of 0–25 amino acids,
   where $K_2$ comprises TFPI Kunitz-type domain 2, or TFPI-2 Kunitz-type domain 2;
   wherein a, b are integers from 0–6;
   wherein A, B, C, D, E, F, G may comprise portions of native TFPI or TFPI-2 sequences or non-native sequence; and
   and the molecule is not native TFPI or TFPI-2.

3. The chimeric protein of claim 2, wherein A or C comprises Kunitz-type domain 3 of TFPI.

4. The chimeric protein of claim 2, wherein A or C comprises Kunitz-type domain 3 of TFPI-2.

5. The chimeric protein of claim 2, wherein at least one of said flanking peptides comprises an amino acid sequence that binds one or more cell surface components.

6. The chimeric protein of claim 5, wherein said amino acid sequence that binds one or more cell surface components is an amino acid sequence that binds a glycosaminoglycan.

7. The chimeric protein of claim 6, wherein said amino acid sequence that binds a glycosaminoglycan is an amino acid sequence that binds heparin.

8. The chimeric protein of claim 7, wherein said amino acid sequence that binds heparin is a heparin-binding domain from a protein, said protein selected from the group consisting of:
   (a) protease nexin-1;
   (b) protease nexin-2;
   (c) antithrombin III;
   (d) heparin cofactor II;
   (e) protein C inhibitor;
   (f) platelet factor 4;
   (g) bovine pancreatic trypsin inhibitor; and
   (h) ghilanten-related inhibitors.

9. The chimeric protein of claim 7, wherein said amino acid sequence that binds heparin is a heparin-binding domain selected from the group consisting of:

(a) SEQ ID NO: 10;
(b) SEQ ID NO: 11;
(c) SEQ ID NO: 12;
(d) SEQ ID NO: 13;
(e) SEQ ID NO: 14;
(f) SEQ ID NO: 15;
(g) SEQ ID NO: 16;
(h) SEQ ID NO: 17; and
(i) SEQ ID NO: 18.

10. The chimeric protein of claim 5, wherein said flanking peptide comprises the C-terminal tail of TFPI [SEQ ID NO: 7].

11. The chimeric protein of claim 5, wherein said flanking peptide comprises the C-terminal tail of TFPI-2 [SEQ ID NO: 8].

12. The chimeric protein of claim 2, wherein each $K_1$ is Kunitz-type domain 1 of TFPI-2, each $K_2$ is Kunitz-type domain 2 of TFPI, and a and b are integers greater than 1.

13. The chimeric protein of claim, wherein said chimeric protein is represented by the generic structure:

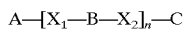

A—[X$_1$—B—X$_2$]$_n$—C wherein A and C are optional flanking peptides, the flanking peptides independently containing 0–100 amino acids;

wherein B is an optional spacer peptide, the spacer peptide containing 0–25 amino acids;

wherein each $X_1$ is —D—$K_1$—E— where D, E are independently peptides of 0–25 amino acids, where $K_1$ is Kunitz-type domain 1 from TFPI or TFPI-2;

wherein each $X_2$ is —F—$K_2$—G— where F, G are independently peptides of 0–25 amino acids, where $K_2$ is Kunitz-type domain 2 from TFPI or TFPI-2;

wherein n is an integer from 1–10.

14. The chimeric protein of claim 13, wherein A or C comprises Kunitz-type domain 3 of TFPI [SEQ ID NO: 7].

15. The chimeric protein of claim 13, wherein A or C comprises Kunitz-type domain 3 of TFPI-2 [SEQ ID NO: 8].

16. The chimeric protein of claim 15, wherein said amino acid sequence that binds glycosaminoglycan is an amino acid sequence that binds heparin.

17. The chimeric protein of claim 16, wherein said amino acid sequence that binds heparin is a heparin-binding domain from a protein, said protein selected from the group consisting of:

(a) protease nexin-1;
(b) protease nexin-2;
(c) antithrombin III;
(d) heparin cofactor II;
(e) protein C inhibitor;
(f) platelet factor 4;
(g) bovine pancreatic trypsin inhibitor; and
(h) ghilanten-related inhibitors.

18. A nucleic acid molecule comprising a sequence encoding the chimeric protein of claim 1.

19. An expression vector capable of producing the chimeric protein of claim 1, said expression vector comprising the nucleic acid molecule of claim 18 and expression control sequences compatible with expression of said chimeric protein.

* * * * *